(12) United States Patent
Khatchatrian et al.

(10) Patent No.: US 7,090,839 B2
(45) Date of Patent: Aug. 15, 2006

(54) METHOD OF TREATMENT OF HUMAN IMMUNODEFICIENCY DISEASES

(75) Inventors: Ashot P. Khatchatrian, Glendale, CA (US); Robert G. Khatchatrian, Glendale, CA (US)

(73) Assignee: Hidden Valley, N.V., Curacao (AN)

( * ) Notice: Subject to any disclaimer, the term of this patent is extended or adjusted under 35 U.S.C. 154(b) by 0 days.

(21) Appl. No.: 10/348,341

(22) Filed: Jan. 21, 2003

(65) Prior Publication Data

US 2004/0047839 A1  Mar. 11, 2004

Related U.S. Application Data

(63) Continuation of application No. 09/654,287, filed on Sep. 1, 2000, now abandoned.

(51) Int. Cl.
*A61K 45/00* (2006.01)
*A61L 9/04* (2006.01)

(52) U.S. Cl. ........................ 424/93.4; 424/45

(58) Field of Classification Search ............... 424/93.3, 424/93.4, 45; 514/568, 570
See application file for complete search history.

(56) References Cited

U.S. PATENT DOCUMENTS

| 5,077,063 | A | * | 12/1991 | Nikitenko | .................... 426/42 |
|---|---|---|---|---|---|
| 5,853,738 | A | | 12/1998 | Istrate et al. | |
| 5,877,213 | A | | 3/1999 | Samid | |
| 5,888,511 | A | | 3/1999 | Skurkovich et al. | |
| 6,056,978 | A | * | 5/2000 | Beck et al. | .................. 424/535 |

FOREIGN PATENT DOCUMENTS

| EP | 0 362 162 B1 | | 3/1992 |
|---|---|---|---|
| RU | 2077886 | | 4/1997 |
| RU | 2089194 | | 10/1997 |
| RU | 2092167 | | 10/1997 |
| RU | 2149633 C1 | | 5/2000 |
| SU | 1717145 A1 | * | 3/1992 |
| SU | 1743532 A1 | * | 6/1992 |
| WO | WO 01/15710 | | 3/2001 |

OTHER PUBLICATIONS

*The Merck Index*, Budavari, Editor, Merck & Co., Inc., Publisher, 1989, p. 1658.

* cited by examiner

*Primary Examiner*—Ralph Gitomer
*Assistant Examiner*—Kailash C. Srivastava
(74) *Attorney, Agent, or Firm*—Knobbe, Martens, Olson & Bear, L.L.P.

(57) ABSTRACT

The present invention relates to a method of treating human immunodeficiency diseases with electroactivated aqueous salt solutions followed by reconstitution of a healthy microflora.

10 Claims, No Drawings

METHOD OF TREATMENT OF HUMAN IMMUNODEFICIENCY DISEASES

RELATED APPLICATIONS

This application is a continuation of U.S. non-provosional application Ser. No. 09/654,287, filed Sep. 1, 2000, now abandoned.

BACKGROUND OF THE INVENTION

1. Field of the Invention

The present invention relates to a method of treating human immunodeficiency diseases with electroactivated aqueous salt solutions followed by reconstitution of a healthy microflora.

2. Description of the Related Art

Acquired immune deficiency syndrome is a disease of the human immune system. The immunodeficient state is reflected in an inability of the immune system to respond to various antigens. The immunodeficient state may allow for the growth of tumors, due to a defect in the normal antitumor activity of the immune system. The immunodeficient state may also lead to allergic or autoimmune problems. The development of an immunodeficient state is often caused by metabolic disorders. These metabolic disorders may result from diabetes, obesity, artherosclerosis, uremia and attrition.

Irritable colon syndrome is a common aspect of many diseases and is often connected with problems in the immune system. Many diseases that appear unrelated, such as AIDS, chronic renal failure, bacterial endocarditis, and bronchial asthma are related by a unified feature: irritable colon syndrome, a common disruption of the balance of microflora in the intestine and growth of pathogenic bacteria. The disruption of the balance of microflora, followed by disruption of the immune system, determines the onset and course of many diseases.

Thus, novel methods of treatment of immunodeficient states can be achieved through the development of new methods of purifying an organism from pathogenic accumulations, normalizing metabolism, and restoring the healthy intestinal microflora. Such methods would make it possible for a person to control the illness by a natural means.

A number of methods of treating immunodeficient states are known. In one, a hexapeptide drug is administered through hypodermic injections. (Patent of Russian Federation No. 2062096). This drug has shown good results in the treatment of immunodeficient patients with chronic and active persistent hepatitis B, brucellosis and chronic bronchitis.

In another method, patients suffering from AIDS or AIDS-related syndromes are treated by the injection of a pharmaceutical composition containing zidovudin (31-azid-31-deoxythymidine) and inosyplex (paracyd-benzoic acid), possibly in combination with inosinum. (European Patent No. 0362162).

Unfortunately, the positive results obtained through these two methods are accompanied by side effects that can lead to damage of the liver, kidney and heart, resulting in severe complications. In addition, these methods do not restore the healthy microflora of the intestine, which has been disrupted by the disease being treated.

Another method of treating immunodeficient patients uses a solution of water mixed with either sodium hydrocarbonate, alcohol solution of iodine, potassium permanganate or sulficil-sodium. In the course of treatment, the patient takes the mixture orally and by means of rectal or vaginal lavage. (Patent of Russian Federation No. 2077886). This method is based on the removal of pathogenic accumulations and the normalization of the metabolism in a natural way that can be regulated by the patient. However, like the methods described above, this method does not restore the healthy microflora of the intestine.

A method of treating irritable colon syndrome that may also be used to treat immunodeficiencies involves purification of the intestine with enemas. This is followed by the implantation of microflora in the intestine with the help of colonoscopy. Lactobacteria are implanted in the ascending section of the intestine, Bifidobacteria are implanted in the transversal section and colibacteria are implanted in the descending section. (Patent of Russian Federation No. 2092167). Unfortunately, aside from the cleansing enemas, this method does not contemplate removing pathogenic agents from the intestine and thus, is not as effective as it might be.

Another method of treating autoimmune diseases, as well as AIDS, consists of inhibiting, removing or neutralizing a variety of growth factors, antigens or receptors. This treatment comprises either administering the active molecules directly to the patient's blood or removing the patient's blood, treating it, and returning it to the patient. (U.S. Pat. No. 5,888,511).

It is also possible to treat immunological disorders, inflammatory diseases and infections with magnesium gluconate. The magnesium gluconate may be administered alone or in combination with antioxidants or anti-inflammatory agents. (U.S. Pat. No. 5,853,738). Additional methods use pharmacologically accepted salts, such as NaPa alone or in combination with suraminum, interferon or Pag. These agents act directly to suppress the growth of tumor cells and to prevent the onset of problems associated with viral infections. (U.S. Pat. No. 5,877,213).

The inadequacy of the treatment described above is insufficient stimulation of the immune system and a failure to normalize metabolism. Additionally, they do not regenerate the healthy microflora.

Finally, a generalized method of treating viral infections, such as AIDS, herpes and hepatitis, and the accompanying immunodeficiencies has been described. The method is based on a course of therapy consisting of the introduction into the patient of an electroactivated aqueous NaCl solution in an amount that does not exceed the daily requirements for electrolytes and water. Simultaneously, the patient is exposed to dry radon with a frequency of radiation of 17 gHz for 1.5 to 2 minutes. (Patent of Russian Federation No. 2089194). As with the other described methods, this method is problematic because it does not provide sufficient immunostimulation, does not normalize metabolic processes and does not regenerate the healthy microflora.

SUMMARY OF THE INVENTION

The present invention relates to a method of treating humans suffering from a disease. The method comprises rectally administering to said human an electroactivated aqueous salt solution with negative redox potential. This is followed by implantation of bacteria in the intestine to restore a healthy microflora. The method may additionally comprise administering an electroactivated aqueous salt solution with negative redox potential orally or by injection. The method of the present invention may also comprise rinsing the oral cavity, nasopharynx and vaginal cavity with an electroactivated aqueous salt solution with positive redox potential.

DETAILED DESCRIPTION OF THE PREFERRED EMBODIMENT

The method of the present invention is a preventative and treatment for immunodeficiencies. The aim of the present invention is to provide a more effective method to prevent and treat immune diseases through intensive decontamination and the restoration of the microflora found in the healthy individual (healthy microflora).

The method of the present invention comprises a course of treatment. The first step comprises the administration of electroactivated aqueous salt solutions to the patient. Preferably the volume of electroactivated aqueous salt solution administered does not exceed the daily requirements for electrolytes and water.

Aqueous solutions of salts with negative or positive redox potential are activated by any method known in the art. Preferably they are activated on a membranous electrolyzer. Any membranous electrolyzer known in the art may be used. For example, a membranous electrolyzer of the Espero type may be used. For aqueous salt solutions with negative redox potential, the measured values are preferably −300 to −1200 mV and pH 8.0 to 12.0. More preferably, the measured values are −500 to −900 mV and pH 9.0 to 11.0. For aqueous salt solutions with positive redox potential, the measured values are preferably +500 to +1200 mV and pH 0.05 to 5.0. More preferably the measured values are +900 to +1200 and pH 1.0 to 2.0.

For the aqueous salt solutions, the salt may be any salt know in the art. However, the salt is preferably either $AgNO_3$, in a density of no more than 14 grams/liter or a mixture of the salts NaCl, KCl, $CaCl_2$ and $MgCl_2$, in any ratio and at a density of no more than 15 grams/liter. More preferably the salt is either $AgNO_3$ in a density of no more than 7 grams/liter or the salts NaCl, KCl, $CaCl_2$ and $MgCl_2$ in the same ratio as they are found in the plasma (80:2:2:1) and at a density of no more than 10 grams/liter.

The electroactivated aqueous solution of salts with negative redox potential is administered to the patient through three separate routes. First, it is administered to the patient by way of intravenous injection of preferably no more than 400 ml per day. More preferably no more than 200 ml/day is administered.

Second, it is administered orally, in an amount of no more than 600 ml per day, for 40 days. More preferably it is administered orally before a meal in an amount of no more than 300 ml per day for 15 to 20 days.

Finally, it is administered by way of cleansing enemas, preferably in an amount of 3 liters, twice a day. More preferably it is administered by enema in an amount of 0.5 to 1.5 liters, once per day.

The electroactivated aqueous solution of salts with positive redox potential is also administered to the patient in a number of ways. First, it is administered as an aerosol with a particle size of no more than 10 microns. More preferably, it is administered as an aerosol with a particle size of no more than 3.5 microns. The aerosol is inhaled through the nose or mouth. Preferably, 1 to 10 ml are inhaled four times per day. More preferably, 1 to 3 ml are inhaled twice a day, once in the morning and once in the evening.

Second, in female patients it is administered by way of rinsing vaginal cavity with an amount of 10 to 800 ml four times per day. More preferably, it is administered by this route twice a day in an amount of 200 to 400 ml.

Finally, it is administered by way of rinsing the oral cavity and nasopharynx with an amount of 10 to 800 ml four times per day. More preferably it is administered by this route twice a day in an amount of 200 to 400 ml.

After preliminary cleansing of the intestine through the enemas described above, the healthy microflora is restored. To restore the healthy microflora, bacteria are implanted in the intestine with the aid of a colonoscopy. Any bacteria known in the art may be implanted following any procedure known in the art. Preferably, lactobacteria, bifidobacteria and colibacteria are implanted in the following manner. First, a culture of lactobacteria is implanted in the ascending section of the intestine through a biopsy canal. Second, a culture of bifidobacteria is implanted in the transverse section of colon. Third, a culture of colibacteria is implanted in the descending section of colon. In each section not less than 100 ml of liquid culture is administered. More preferably, not less than 20 ml is administered. The implanted bacteria may be in any phase of growth and the titer is not less than $10^4$ units/ml. More preferably, the bacteria is in the log phase of growth and the titer is not less than $10^8$ units/ml.

In female patients, healthy microflora is also restored in the urogenital tract. After rinsing the vaginal cavity as described above, liquid lactobacteria is are implanted in the vagina. Preferably not more than 20 ml is implanted. More preferably 5 to 10 ml is implanted. The implanted bacteria may be in any phase of growth and the titer is not less than $10^4$ units/ml. More preferably, the bacteria is in the log phase of growth and the titer is not less than $10^8$ units/ml.

Healthy microflora is also restored in the oral cavity and nasopharynx. Following rinsing of the oral cavity and nasopharynx, liquid lactobacteria culture is applied. The applied bacteria may be in any phase of growth and the titer is not less than $10^4$ units/ml. More preferably the bacteria are in the log phase of growth and the titer is not less than $10^8$ units/ml. From 1 to 10 ml are applied through the oral cavity and from 0.1 to 4 ml through the nose. More preferably, from 3 to 5 ml are applied through the oral cavity and from 1 to 2 ml through the nose.

Experimental research has shown that when an electric current is passed through the aqueous salt solution in the membranous electrolyzer, the molecules, atoms and ions are electroactivated and the ions are redistributed in the electric field. As a result, a portion of the aqueous solution in the cathode zone (catolite) acquires restorative properties and maintains a potential energy. A high biological activity is observed with electroactivated aqueous salt solution in a range of from −400 to −900 mV and pH 7.5 to 11. Application of the activated solution increases the electrochemical processes in living cells. It accelerates all natural biological processes, including regeneration of cells and tissues and immune processes. The catolite has an immunostimulating, detoxifying ability, which acts to normalize the metabolic process in an organism. In addition, the catolite has some bacteriostatic properties.

Electrolyzing aqueous salt solution also produces solution with a positive redox potential. The aqueous solution with a positive redox potential of +900 to +1200 mV and pH 1.0 to 2.0 (anolite), has antiseptic, antiflammatory and antiproliferative properties.

For the correction of the healthy microflora, any bacterial strains known in the art may be used. The following strains are preferable: *Bifidobacterium bifidum* 1 or 791; *Bifidobacterium longum* 397; *Bifidobacterium adolescentis* MC-42; and *Lactobacillus acidophilus* 317/402. The Bifidobacteria and Lactobacteria are the main components of the microflora of the intestine and urogenital tract of humans. These bacteria are antagonistic to many agents that cause intestinal and urogenital infection, stimulate self-protective mechanisms and increase resistance to many diseases.

One example of a strain of *Lactobacillus acidophilus* that may be used in the present invention is Strain 317/402, known as "Narine." This strain synthesizes vitamins such as folic acid, thiamin and riboflavin. It also induces the production of interferon, which increases the strain's beneficial properties.

Combining drug therapy with regeneration of healthy microflora increases the effectiveness of treatment. Oral, vaginal and rectal administration of bacteria combined with the use of pharmacologically active solutions improves the ability to destroy pathogenic microflora in the intestine and urogenital tract and restore a healthy microflora. The implanted bacteria compete with the pathogenic microflora for binding sites on the epithelial cells of the intestine and urogenital tract, thus, displacing the pathogenic microflora and allowing for the development of a healthy microflora.

EXAMPLE 1

An activated aqueous solution of silver salt, both anolite and catolite, was prepared by placing 10 liters of 0.9% $AgNO_3$ solution in an Espero membranous electrolyzer. After 15 to 20 minutes, 2 liters of salt solution was removed from the chamber containing the catolite. This solution had a negative redox potential of −700 mV at pH 8.0 and was poured into a hermetically sealed container and stored without an air layer in a dark place. From the chamber containing the anolite, 8 liters with positive redox potential of +1000 mV at pH 1.5 was removed and poured into a hermetically closed container and stored without an air layer in a dark place.

EXAMPLE 2 to prepare an electroactivated aqueous solution of an admixture of salts, 10 liters of a 1.0% solution of NaCl, KCl, $CaCl_2$ and $MgCl_2$ in a ratio of 80:2:2:11 was poured into an Espero membranous electrolyzer. After 30 to 35 minutes, 2 liters of activated aqueous solution was taken from the chamber containing the catolite. This solution had a negative redox potential of −900 mV at a pH of 11.0. It was poured into a hermetically sealed container and stored without an air layer in the dark. From the chamber containing the anolite, 8 liters with positive redox potential of +1100 mV at pH 1.0 was removed and poured into a hermetically sealed container. It was stored without an air layer in the dark.

EXAMPLE 3

An inoculating dose of *Bifidobacterium bifidum*, strain 791, was added to a nutrient medium, based on skim milk, that contained the components of yeast autosylate. The inoculating dose was 3 to 5% by mass, with a titer of $7\times10^7$ units/ml. This culture was grown at 37° C. for 18 to 24 hours, until it formed a dense biomass of bacteria that were in the log phase of growth. The acidity of the resulting culture was approximately 100° T and the titer of cells was 7 to $9\times10^9$ units/ml.

EXAMPLE 4

A nutrient medium was prepared, based on skim milk, that contained the components of yeast autosylate, maize extract and ascorbic acid. An inoculating dose of *Bifidobacterium adolescentis* strain MC-42 was added to the medium in an amount of 5% by volume, with a titer of $10^8$ units/ml. After mixing, the culture was grown at 38° C. for 12 hours, producing a dense, even culture in the log phase of growth with a titer of 1 to $3\times10^{10}$ units/ml and an acidity of 100° T. At this point the culture was cooled to 25° C. and oxidized to 50 to 80° T.

EXAMPLE 5

A sterile nutritive medium was made based on milk and containing sodium citrate in an amount of 0.1 to 0.3 to $10^{-2}$% by mass. The sour of a culture of *Lactobacillus acidophilus* strain 317/402 was added in an amount of 2 to 5% by mass. The culture was grown at 38° C. for 4 to 6 hours, until the bacteria were in the log phase of growth. The resulting culture was maintained in the refrigerator at 5 to 8° C. for at least 2 hours. The titer of the bacteria in the liquid product was 2 to $4\times10^9$ units/ml.

EXAMPLE 6

An inoculating dose of *Escherichia coli* was introduced onto blood agar with polymyxin and grown to a culture with a titer of not less than $10^8$ units/ml. The culture was separated from the nutrient medium after the bacteria had entered the log phase of growth.

The first step in the medical treatment of a patient is the diagnosis of the disease and an investigation of the status of the microflora in the institute, urogenital tract and oral cavity. A special treatment regimen is developed for each patient, depending on this diagnosis and investigation.

EXAMPLE 7

The electroactivated aqueous salt solution with negative redox potential can be administered to treat a patient with a weakened immune system and without obvious signs of irritable colon. The weakened immune system may be caused by, for example, catarrhal diseases, herpes, etc. The aqueous salt solution with negative redox potential may be administered in one or two intravenous injections per day, totaling no more than 200 ml. This treatment is preferably continued for 7 to 10 days. In another example, 300 ml of this solution may be administered orally before meals for 15 to 20 days.

In addition, the electroactivated aqueous salt solution with positive redox potential may be administered as an aerosol with particle size of no more than 3.5 microns. From 1 to 3 ml of the aerosol is preferably administered by way of inhalation into the respiratory tract either orally or through the nose twice a day, in the morning and the evening.

EXAMPLE 8

The method of the present invention can also be used to treat patient suffering from generalized viral infections, such as AIDS or hepatitis, who also show symptoms of secondary immunodeficiencies and some disruption of the healthy microflora. The electroactivated aqueous salt solution with negative redox potential, prepared as in Examples 1 or 2, is first administered by intravenous injections. Preferably no more than 200 ml per day is administered for the first 7 to 10 days and the treatment should not be continued for more than 15 to 20 days, depending on the health of the patient.

Within several days of beginning the treatment, the intestine of the patient is preferably cleaned with enemas comprising electroactivated aqueous salt solution with negative redox potential, prepared as in Examples 1 or 2. Preferably, 0.5 to 1.5 liters of this solution is administered once per day, in any manner known in the art.

In addition, the patient rinses the oral cavity and nasopharynx twice a day with 100 to 200 ml of the electroactivated aqueous salt solution with positive redox potential, produced as in Examples 1 and 2. Female patients also carry out vaginal washes twice a day with 200 ml of the electroactivated aqueous salt solution.

These treatments are followed by the implantation of intestinal microflora, with the assistance of a colonoscopy. A culture of Lactobacteria as prepared in Example 5 is placed in the ascending section of the intestine through a biopsy canal. A culture of Bifidobacteria prepared as in Example 3 or 4 is placed in the transverse section of the intestine. A culture of E. coli prepared as in Example 6 is placed in the descending section of the large intestine. In each placement, not less than 20 ml of culture is used.

Finally, after the treatment of the oral cavity and nasopharynx with electroactivated aqueous solution is completed, liquid Lactobacteria cultures are applied to this area. Approximately 3 to 5 ml of culture are applied orally and 1 to 2 ml through the nose. In addition, for female patients, 5 to 10 ml of liquid Lactobacteria are applied to the vagina after the completion of the treatment with the electroactivated aqueous solution.

EXAMPLE 9

The effect of the treatment was studied on patients with chronic fatigue syndrome. The study consisted of 120 patients, 70% of whom were active women between the ages of 28 and 45 years old. The diagnosis of chronic fatigue syndrome was made based on a complex of a minimum of 8 symptoms that are typical for this disease. These included constant fatigue, insomnia, pain in the muscles and joints, headaches of unknown origin, poor appetite, flaccidity, low grade fever, dyspepsia, and diarrhea or constipation. All patients were subjected to the same tests: blood count, urinalysis, immunological blood analysis and expanded bacteriological analysis of the feces.

The fecal analysis revealed destruction of the healthy intestinal microflora in all patients. This was diagnosed as irritable colon syndrome of the III or IV degree, characterized by a sharp decrease in the amount of *bacillus* in the colon and the almost complete absence of Bifidoflora.

The immunological analysis of nearly all of the patients revealed various problems with the immune system. These problems were characterized by a decrease in the blood level of serum antibodies IgG, type G2, glycoproteins and lysozyme. A low level of hemoglobin (70 to 100 g/l) in the blood was observed in 45% of the patients. The urinalysis showed no deviations from that expected for healthy patients.

Treatment was carried out as described in Example 8. Within 2 weeks of beginning the treatment, the symptoms of chronic fatigue syndrome disappeared and the levels of hemoglobin, serum antibodies, and other immunological measures were normalized.

EXAMPLE 10

Two patients, A, a 37 year-old woman and P, a 40 year-old woman, were diagnosed with acute diffused psoriasis and candidiasis. In addition, both patients suffered from irritable colon syndrome and disbacteriosis of the urogenital tract. The diagnosis of candidiasis was made by the detection of candidia in the smear. In addition, immunological blood analysis revealed reduced levels of hemoglobin and serum antibodies.

Patient A's urogenital tract problem was treated by conventional antibiotic therapy. The psoriasis was treated with desensitizing drugs (calcium chlorate or calcium gluconate), sedative drugs (tincture araliae of valeriana or herb of leonurus), antihistamine drugs (dimedrolum, suprstinum, diazolinum), vitamins and other pharmacological preparations. The localized areas of psoriasis were treated conventionally with anti-inflammatories, hormonal drugs, keratolytic creams and unguents.

Patient P was treated by the method of the present invention. The electroactivated aqueous salt solution with negative redox potential prepared as in Example 1 or 2 was given orally before a meal in an amount of not more than 300 ml per day for 15 days. Within several days of beginning this treatment, the intestine was cleansed once per day with an enema of 0.5 to 1.5 liters of the electroactivated aqueous salt solution with negative redox potential, prepared as in Example 1 or 2.

The oral cavity and nasopharynx were rinsed with 100 to 200 ml of electroactivated aqueous salt solution with a positive redox potential prepared as in Example 1 or 2. This was done twice a day. In addition, the vagina was washed twice a day with 200 ml of the electroactivated aqueous salt solution with positive redox potential prepared as in Example 1 or 2.

After the preliminary cleansing of the intestine as described above, intestinal microflora was implanted with the assistance of a colonoscopy. A culture of Lactobacteria as prepared in Example 5 was placed in the ascending section of the intestine through a biopsy canal. A culture of Bifidobacteria prepared as in Example 3 or 4 was placed in the transverse section of the intestine. A culture of *E. coli* prepared as in Example 6 was placed in the descending section of the large intestine. In each case, not less than 20 ml of the culture was placed. The bacteria in the cultures were in the log phase of growth and at a titer of not less than $10^8$ units/ml.

Finally, after the treatment of the oral and vaginal cavities with electroactivated aqueous solution was completed, liquid *Lactobacteria* cultures were applied to these areas. Approximately 3 to 5 ml of culture were applied orally and 1 to 2 ml through the nose. In addition, 5 to 10 ml of liquid Lactobacteria were applied to the vaginal cavity. Lastly, the skin surface was wiped with electroactivated aqueous salt solution with positive redox potential prepared pursuant to Example 1 or 2.

After 2 months of treatment, both patients were examined. In the first patient, candidiasis was again diagnosed and after a period of remission, the signs of psoriasis were beginning to reappear. This patient continued to suffer intestinal dysbacteriosis.

The second patient, treated according to the method of the present invention, showed remission of all problems and the symptoms of psoriasis had not reappeared after 6 months.

EXAMPLE 11

Patient C was diagnosed with AIDS. Laboratory tests revealed the following: creatinine 154; common bilirubin 36 mmol/l; urea 7.6; pH 7.55; $pCO_2$ 27.8; $pO_2$ 89.9; VE+2.7; Hb 90 g/l; HT 33; EKA 26.5 g/l. Immunological tests revealed the following: absolute lymphocytes 480 units; T-helpers: T-suppressors 2.0; ATF in lymphocytes of 3.3 units/l (deficit of immunocompetent cells). A microbiological analysis of the feces revealed stage IV dysbacteriosis of the intestine.

A course of treatment was initiated according to the method of the present invention as described in Example 8 above.

Some days after the onset of treatment, positive shifts in the laboratory tests were observed: EKA 33 g/l; urea 5.2; creatinine 115; common bilirubin 11 mmol/l; ALT 16; ACT 32; pH 7.51; $pCO_2$ 35; $pO_2$ 95.0; VE+4.5; Hb 93 g/l; NT 34. In the immunological tests, the numbers had changed as well: absolute number of lymphocytes 1050 units; TLF 43% T-helpers: T-suppressors 1.4; ATF in lymphocytes of 2.5 units/i (imbalance in the system of regulating cells with a background deficit of T-helper cells).

A positive change was observed with the treatment and so the treatment was continued for 21 days. As a result of the treatment the patient was stabilized and an analysis of the patient's blood showed no trace of the AIDS infection.

Thus, the method of the present invention shows considerable ability to treat immunodeficiency disorders in humans.

We claim:

1. A method of treating chronic fatigue syndrome or disbacteriosis in a human, said method comprising:
   electroactivating an aqueous solution of an inorganic salt selected from the group consisting of AgNO3, NaCl, KCl, $CaCl_2$ and $MgCl_2$ to create an electroactivated aqueous inorganic salt solution having a redox potential in the range from −300 mV to −1200 mV and a pH from 8 to 12;
   administering to said human said electroactivated aqueous inorganic salt solution; and
   implanting bacteria in the intestine of said human, wherein said bacteria are selected from the group consisting of lactic acid bacteria, bifidobacteria and *Escherichia coli* bacteria.

2. The method of claim 1, wherein the administering comprises rectally administering to said human said electroactivated aqueous inorganic salt solution.

3. The method of claim 1, wherein said lactic acid bacteria are implanted in the ascending section of the intestine, said bifidobacteria are implanted in the transverse section of the intestine, and said *Escherichia coli* bacteria are implanted in the descending section of the intestine.

4. The method of claim 1, wherein said electroactivated aqueous salt solution has a negative redox potential of −500 to −900 mV and a pH of 9 to 11.

5. The method of claim 1, wherein the salt in said electroactivated aqueous salt solution comprises AgNO3.

6. The method of claim 1, wherein the salt in said electroactivated aqueous salt solution comprises NaCl, KCl, $CaCl_2$ and $MgCl_2$.

7. The method of claim 6, wherein said NaCl, KCl, $CaCl_2$ and $MgCl_2$ are in a ratio of 80:2:2:1.

8. The method of claim 1, additionally comprising rectal cleansing of said human prior to implanting said bacteria in the intestine of said human.

9. The method of claim 8, wherein the rectal cleansing is performed for each of ten days prior to implanting said bacteria in the intestine of said human.

10. The method of claim 8, wherein the rectal cleansing is performed using an electroactivated aqueous salt solution which is the same or different than the electroactivated aqueous inorganic salt solution used in the administering step.

\* \* \* \* \*